(12) United States Patent
Deligianni et al.

(10) Patent No.: US 10,874,876 B2
(45) Date of Patent: Dec. 29, 2020

(54) MULTIPLE LIGHT SOURCES INTEGRATED IN A NEURAL PROBE FOR MULTI-WAVELENGTH ACTIVATION

(71) Applicant: INTERNATIONAL BUSINESS MACHINES CORPORATION, Armonk, NY (US)

(72) Inventors: Hariklia Deligianni, Alpine, NJ (US); Ko-Tao Lee, Yorktown Heights, NY (US); Ning Li, White Plains, NY (US); Devendra K. Sadana, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 311 days.

(21) Appl. No.: 15/881,211

(22) Filed: Jan. 26, 2018

(65) Prior Publication Data
US 2019/0232083 A1    Aug. 1, 2019

(51) Int. Cl.
*A61N 5/06* (2006.01)
*H01L 25/075* (2006.01)
(Continued)

(52) U.S. Cl.
CPC ......... *A61N 5/0622* (2013.01); *A61N 5/0601* (2013.01); *H01L 25/0753* (2013.01);
(Continued)

(58) Field of Classification Search
CPC ... A61B 5/0205; A61B 5/0022; A61B 5/0452; A61B 5/746; A61B 5/681; A61B 5/11; A61B 5/14546; A61B 5/14542; A61B 5/0402; A61B 5/6832; A61B 2562/0219; A61B 5/021; A61B 5/02416; G06F 19/00;
(Continued)

(56) References Cited

U.S. PATENT DOCUMENTS

| 9,653,642 B1* | 5/2017 | Raring .............. H01L 21/6835 |
| 2010/0320450 A1* | 12/2010 | Fujioka .............. C23C 14/0641 257/40 |

(Continued)

FOREIGN PATENT DOCUMENTS

| CN | 106308754 | 1/2017 |
| CN | 106913315 | 7/2017 |

(Continued)

OTHER PUBLICATIONS

Joseph M. Stujenske et al., Modeling the Spatiotemporal Dynamics of Light and Heat Propagation for In Vivo Optogenetics, Cell Reports, Jul. 2015, pp. 525-534.

(Continued)

*Primary Examiner* — Michael W Kahelin
(74) *Attorney, Agent, or Firm* — Tutunjian & Bitetto, P.C.; Randall Bluestone

(57) ABSTRACT

Probes include a probe body configured to penetrate biological tissue. High-efficiency light sources are positioned within the probe body. Each high-efficiency light source has a sufficiently intense light output to trigger a light-sensitive reaction in neighboring tissues and has a sufficiently low power output such that a combined heat output of multiple light sources does cause a disruptive temperature increase in the neighboring tissues.

16 Claims, 3 Drawing Sheets

(51) Int. Cl.
  *H01L 33/00* (2010.01)
  *H01L 33/30* (2010.01)
  *H01L 33/32* (2010.01)

(52) U.S. Cl.
  CPC .......... *A61N 2005/0612* (2013.01); *A61N 2005/0652* (2013.01); *A61N 2005/0659* (2013.01); *A61N 2005/0663* (2013.01); *H01L 33/0012* (2013.01); *H01L 33/0025* (2013.01); *H01L 33/30* (2013.01); *H01L 33/32* (2013.01)

(58) Field of Classification Search
  CPC .......... G16H 40/67; A61N 5/0601; A61N 2005/0612; A61N 5/0622
  See application file for complete search history.

(56) References Cited

U.S. PATENT DOCUMENTS

| | | |
|---|---|---|
| 2014/0024902 A1 | 1/2014 | Mahadevan-Jansen et al. |
| 2014/0200431 A1 | 7/2014 | Jamieson et al. |
| 2014/0324138 A1 | 10/2014 | Wentz et al. |
| 2015/0018901 A1* | 1/2015 | Li .................. A61N 5/0601 607/92 |
| 2015/0133761 A1 | 5/2015 | Vetter et al. |
| 2016/0367836 A1 | 12/2016 | Kampasi et al. |

FOREIGN PATENT DOCUMENTS

| | | |
|---|---|---|
| WO | 2013/093463 | 6/2013 |
| WO | 2015/094076 | 6/2015 |
| WO | 2017/019482 | 2/2017 |

OTHER PUBLICATIONS

Sung Il Park et al., Soft, stretchable, fully implantable miniaturized optoelectronic systems for wireless optogenetics, Nat Biotechnol, Dec. 2015, pp. 1280-1286.

Kwang H. An et al., Organic light-emitting device on a scanning probe cantilever, Applied Physics Letters, Sep. 2006.

Gustavo Rios et al., Nanofabricated Neural Probes for Dense 3-D Recordings of Brain Activity, ACS Publications, Sep. 2016.

Kate L. Montgomery et al., Beyond the brain: Optogenetic control in the spinal cord and peripheral nervous system, Science Translational Medicine, May 2016.

International Search Report and Written Opinion for PCT/IB2019/050291 dated Apr. 17, 2019 (12 pages).

* cited by examiner

MULTIPLE LIGHT SOURCES INTEGRATED IN A NEURAL PROBE FOR MULTI-WAVELENGTH ACTIVATION

BACKGROUND

Technical Field

The present invention generally relates to optogenetics and, more particularly, to neural probes having multiple efficient light sources for activating neurons without overheating local tissue.

Description of the Related Art

The field of optogenetics involves genetically modifying organisms to express sensitivity to light, providing the ability to selectively control neurons in living organisms. Optogenetics thereby provides the ability to directly trigger and observe specific biological processes within an organism.

To accomplish the optical triggering of neurons, a neural probe is used that includes, for example, a light emitting diode. The light emitting diode illuminates nearby neurons, causing those neurons to activate. However, this technique is limited by the generation of heat in the light emitting diode. In particular, a temperature increase of as little as 2° C. can compromise the behavior of the neural tissue.

SUMMARY

A probe includes a probe body configured to penetrate biological tissue. High-efficiency light sources are positioned within the probe body. Each high-efficiency light source has a sufficiently intense light output to trigger a light-sensitive reaction in neighboring tissues and has a sufficiently low power output such that a combined heat output of multiple light sources does cause a disruptive temperature increase in the neighboring tissues.

A probe includes a probe body configured to penetrate biological tissue. High-efficiency light emanating diodes (LEDs) are disposed within the probe body. At least one LED outputs light in a red or infrared portion of the electromagnetic spectrum and at least one LED outputs light in a blue, yellow, or green portion of the electromagnetic spectrum. Each high-efficiency LED has a sufficiently intense light output to trigger a light-sensitive reaction in neighboring tissues and each LED has a sufficiently low power output, such that a combined heat output of multiple LEDs does cause a disruptive temperature increase in the neighboring tissues.

A probe includes a probe body configured to penetrate biological tissue. High-efficiency light sources are disposed within the probe body. Each high-efficiency light source has a light output of at least 10 mW/mm$^2$ and has a sufficiently low power output such that each of the high-efficiency light sources causes a temperature increase in neighboring tissue between about 0.022° C. and about 0.041° C. when active.

These and other features and advantages will become apparent from the following detailed description of illustrative embodiments thereof, which is to be read in connection with the accompanying drawings.

BRIEF DESCRIPTION OF THE DRAWINGS

The following description will provide details of preferred embodiments with reference to the following figures wherein.

DETAILED DESCRIPTION

Embodiments of the present invention provide neural probes with highly efficient light sources. These efficient light sources produce less heat than conventional light emitting diodes, making it possible to include multiple such light sources on a single probe, each emitting a different wavelength. As a result, multiple different wavelength sensitivities can be used at once, providing the ability to selectively activate different sets of neurons with a single probe without causing disruptive increases in tissue temperature.

Figure 1:
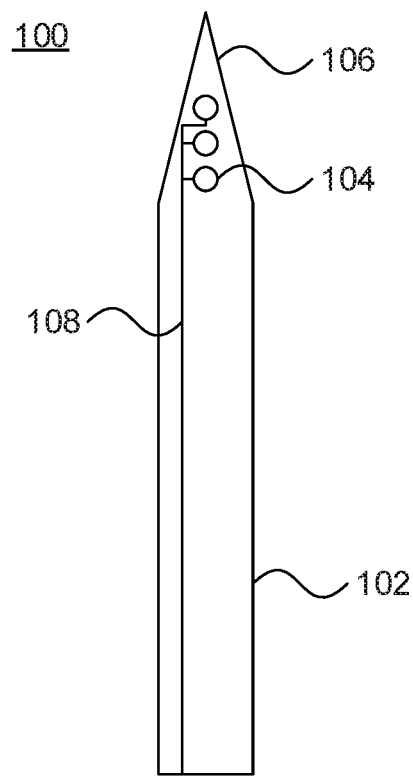
FIG. 1 is a diagram of a neural probe having multiple high-efficiency light sources in accordance with an embodiment of the present invention.

Referring now to the drawings in which like numerals represent the same or similar elements and initially to FIG. 1, a neural probe 100 is shown. The probe 100 includes a probe body 102 with multiple high-efficiency light sources 104. It should be understood that the light sources 104 may be of any appropriate type and at any appropriate location along the length of the probe body 102, but it is specifically contemplated that the light sources 104 may be formed as high-efficiency light emitting diodes (LEDs) near the probe tip 106. Control/power lines 108 are shown as well and provide a current to power the light sources 104, as well as optionally providing control signals to the light sources 104.

It should be understood that the probe 102 may be constructed of any appropriate biocompatible material, including for example glass, sapphire, or titanium, and is of a shape and size configured to penetrate living biological tissue. The light sources 104 and control/power lines 108 may be attached to the probe 100 by any appropriate biocompatible mechanism (e.g., glue or cement) and may, in some embodiments be fabricated in place on the probe 100. In an alternative embodiment, the probe 102 may be formed on a printed circuit board that is then encased in a transparent biocompatible material to allow light from the light sources 104 to reach surrounding tissues. It is specifically contemplated that the probe 100 is designed to penetrate living tissues, in particular neural tissue. Thus the diameter of the probe 100 should be quite small and the probe point 106 should be sharp. Furthermore, the probe body 102 should be made with sufficient durability to penetrate such tissues without being damaged in the process.

Different neural tissues have been engineered to be activated by different wavelengths and at different light intensities. Exemplary wavelengths for the light sources 104 range from about 1850 nm to about 2120 nm, though it should be understood that wavelengths above or below this range may also be used. A stimulation threshold represents the energy density needed to activate a neuron and may be between about 1.6 mJ/cm$^2$ and about 16904 mJ/cm$^2$, depending on the type of neuron. The light can be used to trigger changes in proteins that modulate membrane potentials in the cells through excitatory or inhibitory membrane currents. This ability to modulate cells has proven instrumental in preclinical studies and holds enormous potential for the treatment of diseases such as Parkinson's, epilepsy, chronic pain, addiction, and depression, among others. It should be understood that the present probe 100 may be used in humans as well as in other animals.

Figure 2:
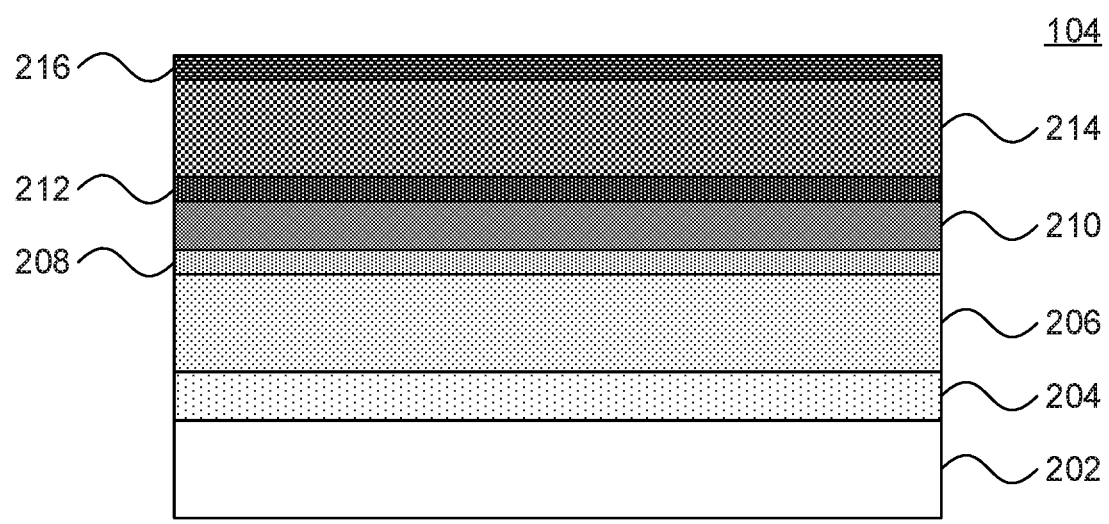
FIG. 2 is a cross-sectional diagram of a high-efficiency light source in accordance with an embodiment of the present invention.

Referring now to FIG. 2, an exemplary structure for the light sources 104 is shown. In this embodiment, the light source 104 is implemented as a low-power LED. The layers of the light source 104 may be deposited sequentially by any appropriate deposition process including, for example, chemical vapor deposition (CVD), physical vapor deposition (PVD), atomic layer deposition (ALD), or gas cluster ion beam (GCIB) deposition.

CVD is a deposition process in which a deposited species is formed as a result of chemical reaction between gaseous reactants at greater than room temperature (e.g., from about 25° C. about 900° C.). The solid product of the reaction is deposited on the surface on which a film, coating, or layer of the solid product is to be formed. Variations of CVD processes include, but are not limited to, Atmospheric Pressure CVD (APCVD), Low Pressure CVD (LPCVD), Plasma Enhanced CVD (PECVD), and Metal-Organic CVD (MOCVD) and combinations thereof may also be employed. In alternative embodiments that use PVD, a sputtering apparatus may include direct-current diode systems, radio frequency sputtering, magnetron sputtering, or ionized metal plasma sputtering. In alternative embodiments that use ALD, chemical precursors react with the surface of a material one at a time to deposit a thin film on the surface. In alternative embodiments that use GCIB deposition, a high-pressure gas is allowed to expand in a vacuum, subsequently condensing into clusters. The clusters can be ionized and directed onto a surface, providing a highly anisotropic deposition.

A semiconductor substrate 202 is formed from an appropriate semiconductor material. In the present embodiments it is specifically contemplated that the semiconductor substrate 202 may be formed from a III-V compound semiconductor material, but it should be understood that a group IV semiconductor material may be used instead. The term "III-V compound semiconductor" denotes a semiconductor material that includes at least one element from Group III of the Periodic Table of Elements (i.e., International Union of Pure and Applied Chemistry (IUPAC) group 13) and at least one element from Group V of the Periodic Table of Elements (i.e., IUPAC group 15). This contrasts to group IV semiconductors which are formed from a single element in group IV of the Periodic Table of Elements (i.e., IUPAC group 14) such as, e.g., silicon, germanium, and compounds thereof. Typically, the III-V compound semiconductors are binary, ternary or quaternary alloys including III/V elements. Examples of III-V compound semiconductors that can be used in the present invention include, but are not limited to alloys of gallium arsenic, aluminum arsenic, indium gallium arsenic, indium aluminum arsenic, indium aluminum arsenic antimony, indium aluminum arsenic phosphorus, indium gallium arsenic phosphorus, cadmium telluride, zinc selenide, and combinations thereof. Examples of group IV semiconductors that can be used in the present invention include, but are not limited to, silicon, germanium, silicon germanium, silicon germanium carbide, silicon carbide, polysilicon, epitaxial silicon, amorphous silicon, and multilayers thereof.

A stack of semiconductor layers are then formed on the semiconductor substrate 202. The stacked layers may be doped according to one of three conductivity types: p-type doped, intrinsic, or n-type doped. The individual layers may be doped by, e.g., ion implantation or they may be doped in situ during deposition. An intrinsic semiconductor material is a material without any dopant. As used herein, "p-type" refers to the addition of impurities to an intrinsic semiconductor that creates deficiencies of valence electrons. In a silicon-containing substrate, examples of p-type dopants, i.e., impurities, include but are not limited to: boron, aluminum, gallium and indium. As used herein, "n-type" refers to the addition of impurities that contributes free electrons to an intrinsic semiconductor. In a silicon containing substrate, examples of n-type dopants, i.e., impurities, include but are not limited to antimony, arsenic and phosphorous. When using III-V compound semiconductor materials, atoms from group II act as acceptors, i.e., p-type, when occupying the site of a group III atom, while atoms in group VI act as donors, i.e., n-type, when they replace atoms from group V. Dopant atoms from group IV, such as silicon, have the property that they can act as acceptors or donor depending on whether they occupy the site of group III or group V atoms respectively.

A highly doped n-type semiconductor layer 204 is formed on the substrate 202. It is specifically contemplated that the highly doped n-type semiconductor layer 204 may be formed from, e.g., gallium arsenide and may have a dopant concentration of about $5 \times 10^{18}$ cm$^{-3}$. An n-type semiconductor layer with a lower dopant concentration 206 is formed on the highly doped n-type semiconductor layer 204 and is formed from indium gallium phosphide with a dopant concentration of about $1 \times 10^{18}$ cm$^{-3}$. The lower-concentration n-type layer 206 has an exemplary thickness of about 200 nm.

A set of intrinsic layers are then formed on the n-type layers 204 and 206. A first intrinsic layer 208 is formed from undoped indium gallium phosphide and has a thickness of about 50 nm. A second intrinsic layer 210 is formed from undoped indium gallium arsenide. A third intrinsic layer 212 is formed from undoped indium gallium phosphide and has a thickness of about 50 nm.

A set of p-type layers are then formed on the intrinsic layers 208, 210, and 212. A first p-type layer 214 is formed on the third intrinsic layer 212 and is formed from p-type doped indium gallium phosphide with a dopant concentration of about $1 \times 10^{18}$ cm$^3$. The first p-type layer has a thickness of about 200 nm. A second, highly-doped p-type layer 216 is formed on the first p-type layer 214 and is formed from p-type doped gallium arsenide with a dopant concentration of about $5 \times 10^{18}$ cm$^{-3}$. The second p-type layer 216 has a thickness of about 30 nm and functions as a top electrical contact for the LED 104.

This LED structure provides a particularly low-power, high-efficiency light source. In particular, the LED has been measured as providing a maximum efficiency in the range between about 1 μA and about 1 mA. In particular, the depicted light source 104 provides an external quantum efficiency between about 0.9 and 1 in this current range. External quantum efficiency measures the ratio of the number of photons emitted from an LED to the number of electrons passing through the device, essentially measuring how efficiently the device converts incoming charges to outgoing photons, with a value of 1 indicating perfect efficiency. As a result of this superior efficiency, the light sources 104 of the present embodiments cause a temperature change in surrounding tissues that is about 100 times smaller than that caused by conventional probes.

Figure 3:
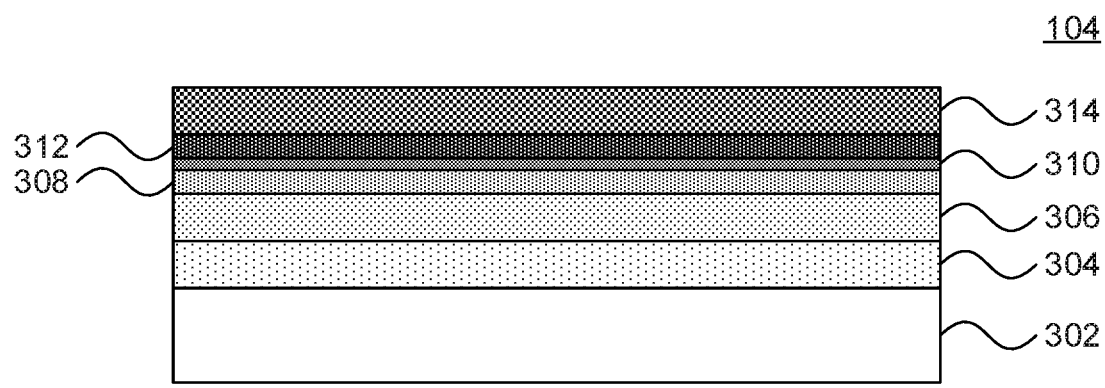
FIG. 3 is a cross-sectional diagram of a high-efficiency light source in accordance with an embodiment of the present invention.

Referring now to FIG. 3, an alternate embodiment of the structure for the light sources 104 is shown. This structure is specifically contemplated for a bio-compatible, highly efficient LED that takes a low injection current and puts out blue, yellow, or green wavelengths (i.e., in blue, yellow, or green portions of the electromagnetic spectrum). As above, the layers of the light source 104 may be deposited sequentially by any appropriate deposition process including, for example, CVD, PVD, ALD, or GCIB deposition. The light source 104 made according to FIG. 3 have high quantum efficiencies roughly equivalent to those obtained by the light source shown in FIG. 2.

A substrate 302 is formed from, e.g., gallium nitride or sapphire (e.g., aluminum oxide) material. A highly n-doped buffer layer 304 is formed on the substrate 302 and may include, for example gallium nitride with a thickness between about 20 nm and about 1,000 nm. The Highly n-doped buffer layer 304 may act as a lower electrical contact for the device. An n-type semiconductor layer 306 is then formed on the buffer layer 304 with a lower dopant concentration than that used in the highly doped buffer layer 304 and with a thickness between about 100 nm and about 1,000 nm. It should be understood that a III-V type semiconductor material such as gallium nitride may use silicon as a dopant, with a dopant concentration on the order of about $1 \cdot 10^{18}$ cm$^3$ to about $1 \cdot 10^{20}$ cm$^{-3}$. A "highly doped" layer will have a greater conductivity due to having a larger number of free charge carriers. Any other appropriate conventional dopant material may be used in the place of silicon.

A set of intrinsic layers are then formed on the n-type layers. A barrier layer 308 may be formed from intrinsic gallium nitride with a thickness between about 20 nm and about 100 nm. A well layer 310 is then formed over the barrier layer 308 from indium gallium nitride (In$_x$Ga$_{(1-x)}$N where x=0.10~0.50) with a thickness of about 2 nm to about 10 nm. A second barrier layer 312 is formed on the well layer 310 from intrinsic gallium nitride with a thickness of about 20 nm to about 100 nm. A p-type layer 314 is then formed on the barrier layer 312 with a thickness between about 100 nm and about 1,000 nm from, e.g., gallium nitride. The top p-type layer 314 may play the role of an upper electrical contact for the device. Any appropriate conventional dopant material may be used to form the p-type doped layers.

In an alternative embodiment, the structure of FIG. 3 may be used with different materials to create a low-power LED which puts out red or infrared wavelengths (i.e., in red or infrared portions of the electromagnetic spectrum). In such an embodiment, the substrate 302 may be formed from germanium. The buffer layer 304 may be formed from highly doped n-type indium gallium phosphorus (In$_{0.49}$Ga$_{0.51}$P) and the lesser-doped n-type semiconductor layer 306 may be formed from In$_{0.49}$Ga$_{0.51}$P having a lower dopant concentration. The first intrinsic barrier layer 308 and the second intrinsic barrier layer 312 may similarly be formed from In$_{0.49}$Ga$_{0.51}$P, while the well layer 310 may be formed from indium gallium phosphorus having a slightly different composition (e.g., In$_x$Ga$_{(1-x)}$P where x=0.50~0.60). The highly doped p-type semiconductor layer 314 may then be formed from In$_{0.49}$Ga$_{0.51}$P.

This embodiment of the light sources 104 uses bio-compatible materials (e.g., gallium nitride or indium gallium phosphorus) and avoids bio-hazardous materials (e.g., arsenic). The output power needed to activate a 100 μm neuron is about 10 mW/mm$^2$. At this power level, the light sources 104 embodied by the structure of FIG. 3 are about 10 to about 100 times more efficient than conventional LEDs, thereby substantially reducing the heating of nearby tissues. In particular, whereas the temperature increase caused by conventional LEDs is about 2.2° C. to about 4.1° C., the temperature increase caused by the present embodiments is about 100 times lower (e.g., about 0.022° C. to about 0.041° C.).

It is to be understood that aspects of the present invention will be described in terms of a given illustrative architecture; however, other architectures, structures, substrate materials and process features and steps can be varied within the scope of aspects of the present invention.

It will also be understood that when an element such as a layer, region or substrate is referred to as being "on" or "over" another element, it can be directly on the other element or intervening elements can also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements can be present. In contrast, when an element is referred to as being "directly connected" or "directly coupled" to another element, there are no intervening elements present.

The present embodiments can include a design for an integrated circuit chip, which can be created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer can transmit the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

Methods as described herein can be used in the fabrication of integrated circuit chips. The resulting integrated circuit chips can be distributed by the fabricator in raw wafer form (that is, as a single wafer that has multiple unpackaged chips), as a bare die, or in a packaged form. In the latter case, the chip is mounted in a single chip package (such as a plastic carrier, with leads that are affixed to a motherboard or other higher level carrier) or in a multichip package (such as a ceramic carrier that has either or both surface interconnections or buried interconnections). In any case, the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

It should also be understood that material compounds will be described in terms of listed elements, e.g., SiGe. These compounds include different proportions of the elements within the compound, e.g., SiGe includes Si$_x$Ge$_{1-x}$ where x is less than or equal to 1, etc. In addition, other elements can be included in the compound and still function in accordance with the present principles. The compounds with additional elements will be referred to herein as alloys.

Reference in the specification to "one embodiment" or "an embodiment", as well as other variations thereof, means that a particular feature, structure, characteristic, and so forth described in connection with the embodiment is included in at least one embodiment. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This can be extended, as readily apparent by one of ordinary skill in this and related arts, for as many items listed.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps operations, elements, components and/or groups thereof.

Spatially relative terms, such as "beneath," "below," "lower," "above," "upper," and the like, can be used herein for ease of description to describe one element's or feature's relationship to another element(s) or feature(s) as illustrated in the FIGS. It will be understood that the spatially relative terms are intended to encompass different orientations of the device in use or operation addition to the orientation depicted in the FIGS. For example, if the device in the FIGS. is turned over, elements described as "below" or "beneath" other elements or features would then be oriented "above" the other e rets or features. Thus, the term "below" can encompass both an ion of above and below. The device can be otherwise oriented (rotated 90 degrees or at other orientations), and the spatially relative descriptors used herein can be interpreted accordingly. In addition, it will also be understood that when a layer is referred to as being "between" two layers, it can be the only layer between the two layers, or one or more intervening layers can also be present.

It will be understood that, although the terms first, second, etc. can be used herein to describe various elements, these elements should not be limited by these terms. These terms are only used to distinguish one element from another element. Thus, a first element discussed below could be termed a second element without departing from the scope of the present concept.

Figure 4:
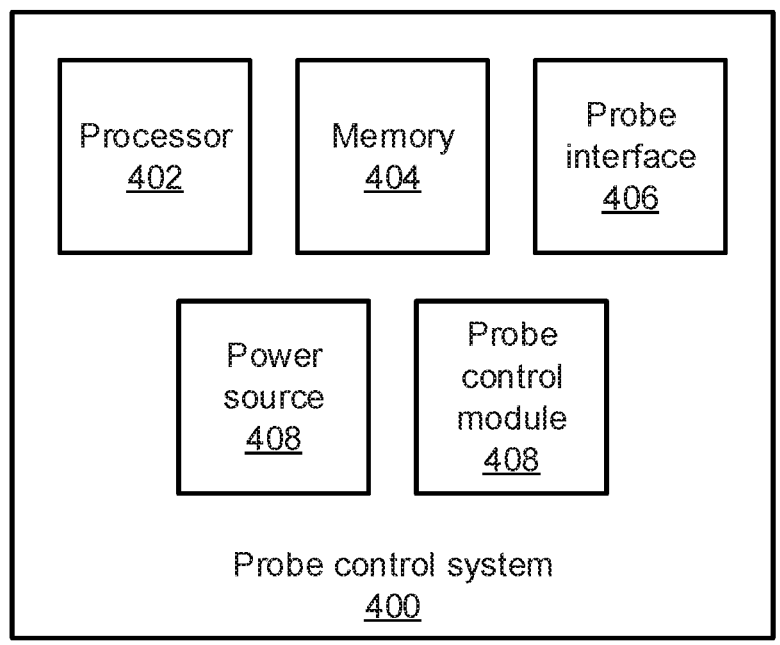
FIG. 4 is a block diagram of a probe control system in accordance with an embodiment of the present invention.

Referring now to FIG. 4, a probe control system 400 is shown. The probe control system 400 includes a hardware processor and memory 404. A probe interface 406 provides a physical communications interface between the probe control system 400 and the probe 100. A power source 408 provides electrical power to the probe 100 via the probe interface 406 and may take the form of a battery or other DC power source or, alternatively, may include suitable circuitry to transform AC power to a form suitable for the probe 100. It is specifically contemplated that the probe interface 406 may have a wired connection to the probe 100 that provides electrical power and control signals, but it is also contemplated that a wireless interface may be used in embodiments where the probe 100 has a local power source. In other embodiments the probe control system 400 may be directly integrated with the body of the probe 100.

A probe control module 408 is, in some embodiments, implemented in the form of software that is stored in the memory 404 and that is executed by the processor 402. In other embodiments, the probe control module 408 may be implemented as one or more discrete hardware components in the form of, e.g., application specific integrated chips or field programmable gate arrays. The probe control module 408 sends command signals to the probe(s) 100 via the probe interface 406 and may be used to activate and deactivate particular light sources 104 and to control their light output. It should be understood that the probe control module 408 may issue these commands at the direction of a human operator or may alternatively issue such commands automatically.

Figure 5:
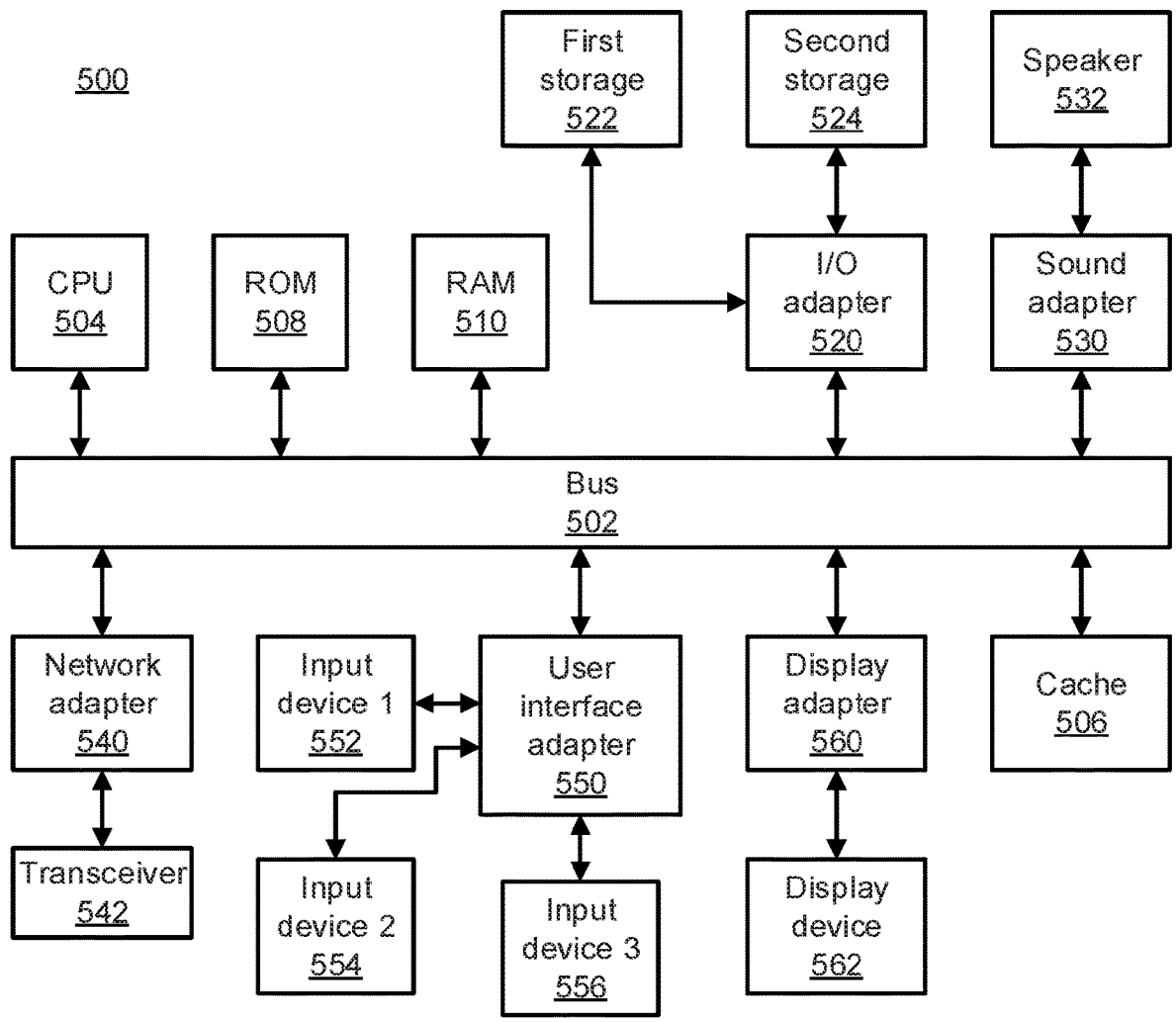
FIG. 5 is a block diagram of a processing system in accordance with an embodiment of the present invention.

Referring now to FIG. 5, an exemplary processing system 500 is shown which may represent the transmitting device 100 or the receiving device 120. The processing system 500 includes at least one processor (CPU) 504 operatively coupled to other components via a system bus 502. A cache 506, a Read Only Memory (ROM) 508, a Random Access Memory (RAM) 510, an input/output (I/O) adapter 520, a sound adapter 530, a network adapter 540, a user interface adapter 550, and a display adapter 560, are operatively coupled to the system bus 502.

A first storage device 522 and a second storage device 524 are operatively coupled to system bus 502 by the I/O adapter 520. The storage devices 522 and 524 can be any of a disk storage device (e.g., a magnetic or optical disk storage device), a solid state magnetic device, and so forth. The storage devices 522 and 524 can be the same type of storage device or different types of storage devices.

A speaker 532 is operatively coupled to system bus 502 by the sound adapter 530. A transceiver 542 is operatively coupled to system bus 502 by network adapter 540. A display device 562 is operatively coupled to system bus 502 by display adapter 560.

A first user input device 552, a second user input device 554, and a third user input device 556 are operatively coupled to system bus 502 by user interface adapter 550. The user input devices 552, 554, and 556 can be any of a keyboard, a mouse, a keypad, an image capture device, a motion sensing device, a microphone, a device incorporating the functionality of at least two of the preceding devices, and so forth. Of course, other types of input devices can also be used, while maintaining the spirit of the present principles. The user input devices 552, 554, and 556 can be the same type of user input device or different types of user input devices. The user input devices 552, 554, and 556 are used to input and output information to and from system 500.

Of course, the processing system 500 may also include other elements (not shown), as readily contemplated by one of skill in the art, as well as omit certain elements. For example, various other input devices and/or output devices can be included in processing system 500, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized as readily appreciated by one of ordinary skill in the art. These and other variations of the processing system 500 are readily contemplated by one of ordinary skill in the art given the teachings of the present principles provided herein.

Having described preferred embodiments of multiple light sources integrated in a neural probe for multi-wavelength activation (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A probe, comprising:
a probe body configured to penetrate biological tissue; and
a plurality of high-efficiency light sources disposed within the probe body, each high-efficiency light source having a light output of at least 10 mW/mm$^2$ and having a sufficiently low power output such that each of the plurality of high-efficiency light sources causes a temperature increase in neighboring tissue that is less than about 0.041° C. when active.

2. The probe of claim 1, wherein the plurality of high-efficiency light sources are light emanating diodes (LEDs).

3. The probe of claim 2, wherein at least one LED outputs light in a red or infrared portion of the electromagnetic spectrum and at least one LED outputs light in a blue, yellow, or green portion of the electromagnetic spectrum.

4. The probe of claim 3, wherein the at least one LED that outputs light in the red or infrared portion of the electromagnetic spectrum comprises:
a germanium substrate;
at least one n-type doped layer of $In_{0.49}Ga_{0.51}P$;
at least one intrinsic layer of $In_{0.49}Ga_{0.51}P$;
a well layer of $In_xGa_{(1-x)}P$, where x is a value between about 0.50 and about 0.60; and
at least one p-type doped layer $In_{0.49}Ga_{0.51}P$.

5. The probe of claim 3, wherein the at least one LED that outputs light in the blue, yellow, or green portion of the electromagnetic spectrum comprises:
a substrate formed from a material selected from the group consisting of gallium nitride and sapphire;
at least one n-type doped layer of gallium nitride;
at least one intrinsic layer of gallium nitride;
a well layer of $In_xGa_{(1-x)}N$, where x is a value between about 0.10 and about 0.50; and
at least one p-type doped layer of gallium nitride.

6. The probe of claim 1, wherein each of the plurality of high-efficiency light sources causes a temperature increase in neighboring tissue between about 0.022° C. and about 0.041° C. when active.

7. The probe of claim 1, wherein each LED has an external quantum efficiency between about 0.9 and 1 in a current range between about 1 μA and about 1 mA.

8. A probe, comprising:
a probe body configured to penetrate biological tissue; and
a plurality of high-efficiency light emanating diodes (LEDs) disposed within the probe body, wherein at least one LED outputs light in a red or infrared portion of the electromagnetic spectrum and at least one LED outputs light in a blue, yellow, or green portion of the electromagnetic spectrum, each high-efficiency LED having a light output of at least 10 mW/mm$^2$ and having a sufficiently low power output such that each of the plurality of high-efficiency light sources causes a temperature increase in neighboring tissue that is less than about 0.041° C. when active.

9. The probe of claim 8, wherein the at least one LED that outputs light in the red or infrared portion of the electromagnetic spectrum comprises:
a germanium substrate;
at least one n-type doped layer of $In_{0.49}Ga_{0.51}P$;
at least one intrinsic layer of $In_{0.49}Ga_{0.51}P$;
a well layer of $In_xGa_{(1-x)}P$, where x is a value between about 0.50 and about 0.60; and
at least one p-type doped layer $In_{0.49}Ga_{0.51}P$.

10. The probe of claim 8, wherein the at least one LED that outputs light in the blue, yellow, or green portion of the electromagnetic spectrum comprises:
a substrate formed from a material selected from the group consisting of gallium nitride and sapphire;
at least one n-type doped layer of gallium nitride;
at least one intrinsic layer of gallium nitride;
a well layer of $In_xGa_{(1-x)}N$, where x is a value between about 0.10 and about 0.50; and
at least one p-type doped layer of gallium nitride.

11. The probe of claim 8, wherein each of the plurality of high-efficiency light sources causes a temperature increase in neighboring tissue between about 0.022° C. and about 0.041° C. when active.

12. The probe of claim 8, wherein each LED has an external quantum efficiency between about 0.9 and 1 in a current range between about 1 μA and about 1 mA.

13. A probe, comprising:
a probe body configured to penetrate biological tissue; and
a plurality of high-efficiency light sources disposed within the probe body, each high-efficiency light source being formed from biocompatible materials and having a sufficiently intense light output to trigger a light-sensitive reaction in neighboring tissues and having a sufficiently low power output such that a combined heat output of multiple light sources does not cause a disruptive temperature increase in the neighboring tissues, wherein at least one LED outputs light in the red or infrared portion of the electromagnetic spectrum and comprises:
a germanium substrate;
at least one n-type doped layer of $In_{0.49}Ga_{0.51}P$;
at least one intrinsic layer of $In_{0.49}Ga_{0.51}P$;
a well layer of $In_xGa_{(1-x)}P$, where x is a value between about 0.50 and about 0.60; and
at least one p-type doped layer $In_{0.49}Ga_{0.51}P$.

14. The probe of claim 13, wherein the substrate has a thickness between about 20 nm and about 100 nm, the well layer has a thickness between about 2 nm and about 10 nm, the intrinsic layer of gallium nitride has a thickness between about 20 nm and about 100 nm, the at least one p-type doped layer has a thickness between about 100 nm and about 1000 nm.

15. A probe, comprising:
a probe body configured to penetrate biological tissue; and
a plurality of high-efficiency light sources disposed within the probe body, each high-efficiency light source being formed from biocompatible materials and having a sufficiently intense light output to trigger a light-sensitive reaction in neighboring tissues and having a sufficiently low power output such that a combined heat output of multiple light sources does not cause a disruptive temperature increase in the neighboring tissues, wherein at least one LED outputs light in the blue, yellow, or green portion of the electromagnetic spectrum comprises:

a substrate formed from a material selected from the group consisting of gallium nitride and sapphire;

at least one n-type doped layer of gallium nitride;

at least one intrinsic layer of gallium nitride;

a well layer of $In_xGa_{(1-x)}N$, where x is a value between about 0.10 and about 0.50; and at least one p-type doped layer of gallium nitride.

16. The probe of claim 15, wherein the substrate has a thickness between about 20 nm and about 100 nm, the well layer has a thickness between about 2 nm and about 10 nm, the intrinsic layer of gallium nitride has a thickness between about 20 nm and about 100 nm, the at least one p-type doped layer has a thickness between about 100 nm and about 1000 nm.

* * * * *